United States Patent
Avellanet

[11] Patent Number: 6,015,415
[45] Date of Patent: Jan. 18, 2000

[54] POLYPECTOMY SNARE INSTRUMENT

[75] Inventor: Francisco J. Avellanet, Coral Gables, Fla.

[73] Assignee: General Science and Technology, Miami, Fla.

[21] Appl. No.: 09/264,772

[22] Filed: Mar. 9, 1999

[51] Int. Cl.[7] .............................. A61B 17/22; A61B 17/38
[52] U.S. Cl. .............................. 606/113; 606/110; 606/47; 606/37
[58] Field of Search ...................................... 606/113, 114, 606/110, 131, 47, 37, 108; 604/22

[56] References Cited

U.S. PATENT DOCUMENTS

| | | | |
|---|---|---|---|
| 3,910,279 | 10/1975 | Okada et al. | 606/47 |
| 3,955,578 | 5/1976 | Chamness et al. | 128/303.15 |
| 4,256,113 | 3/1981 | Chamness | 128/303.14 |
| 4,294,254 | 10/1981 | Chamness | 128/303.14 |
| 5,026,371 | 6/1991 | Rydell et al. | 606/47 |
| 5,098,440 | 3/1992 | Hillstead | 606/108 |
| 5,108,406 | 4/1992 | Lee | 606/106 |
| 5,123,906 | 6/1992 | Kelman | 606/107 |
| 5,147,371 | 9/1992 | Washington et al. | 606/127 |
| 5,158,561 | 10/1992 | Rydell et al. | 606/113 |
| 5,171,233 | 12/1992 | Amplatz et al. | 604/281 |
| 5,190,554 | 3/1993 | Coddington, III et al. | 606/113 |
| 5,192,286 | 3/1993 | Phan et al. | 606/127 |
| 5,201,741 | 4/1993 | Dulebohn | 606/113 |
| 5,290,294 | 3/1994 | Cox et al. | 606/108 |
| 5,354,303 | 10/1994 | Spaeth et al. | 606/128 |
| 5,376,094 | 12/1994 | Kline | 606/113 |
| 5,417,697 | 5/1995 | Wilk et al. | 606/113 |
| 5,535,759 | 7/1996 | Wilk | 128/898 |
| 5,562,678 | 10/1996 | Booker | 606/113 |
| 5,611,803 | 3/1997 | Heaven et al. | 606/114 |
| 5,643,281 | 7/1997 | Suhocki et al. | 606/113 |
| 5,735,289 | 4/1998 | Pfeffer et al. | 128/751 |
| 5,752,961 | 5/1998 | Hill | 606/113 |
| 5,759,187 | 6/1998 | Nakao et al. | 606/114 |
| 5,779,716 | 7/1998 | Cano et al. | 606/114 |
| 5,782,840 | 7/1998 | Nakao | 606/114 |
| 5,788,710 | 8/1998 | Bates et al. | 606/127 |
| 5,814,052 | 9/1998 | Nakao et al. | 606/115 |

OTHER PUBLICATIONS

"Prostate Cancer", by Marc B. Garnick and William R. Fair, article in the Scientific American, Dec. 1998, pp. 75–83.

*Primary Examiner*—Gene Mancene
*Assistant Examiner*—Michael B. Priddy
*Attorney, Agent, or Firm*—David P. Gordon; David S. Jacobson; Thomas A. Gallagher

[57] ABSTRACT

A surgical snare instrument includes a tubular sheath having proximal and distal ends, a flexible shaft having proximal and distal ends extending through and axially movable relative to the sheath, a snare loop at the distal end of the shaft, and a handle assembly coupled to the proximal ends of the sheath and shaft for moving the shaft axially relative to the sheath. The handle assembly is provided with cautery capability to provide a cautery current to the snare loop. The snare loop is trained to have a proximal portion which extends along an angle or curve relative to the tubular member and a distal portion which is substantially parallel to the tubular member. As such, when the snare loop is axially moved beyond the distal end of the sheath, the distal portion of the snare loop; i.e., that portion which is adapted to engage a polyp, is oriented substantially parallel, yet non-axial, with the tubular member. According to one embodiment of the invention, the shaft is torqueable, preferably made from a multifilament twisted and drawn or swaged cable. The handle is preferably additionally adapted to axially rotate the sheath relative to the shaft and the snare loop to facilitate maneuvering the snare loop. According to another embodiment of the invention, the snare loop is provided with a net element adapted to capture a polyp severed by the snare loop.

23 Claims, 5 Drawing Sheets

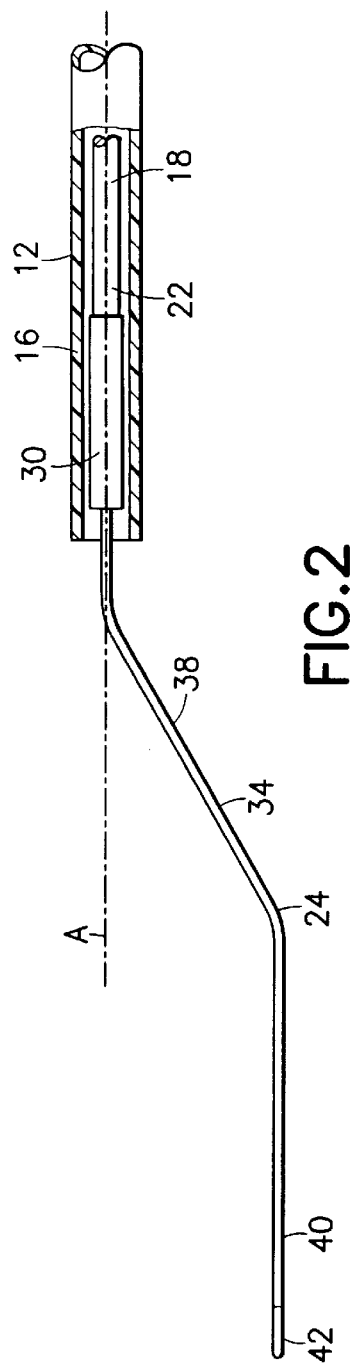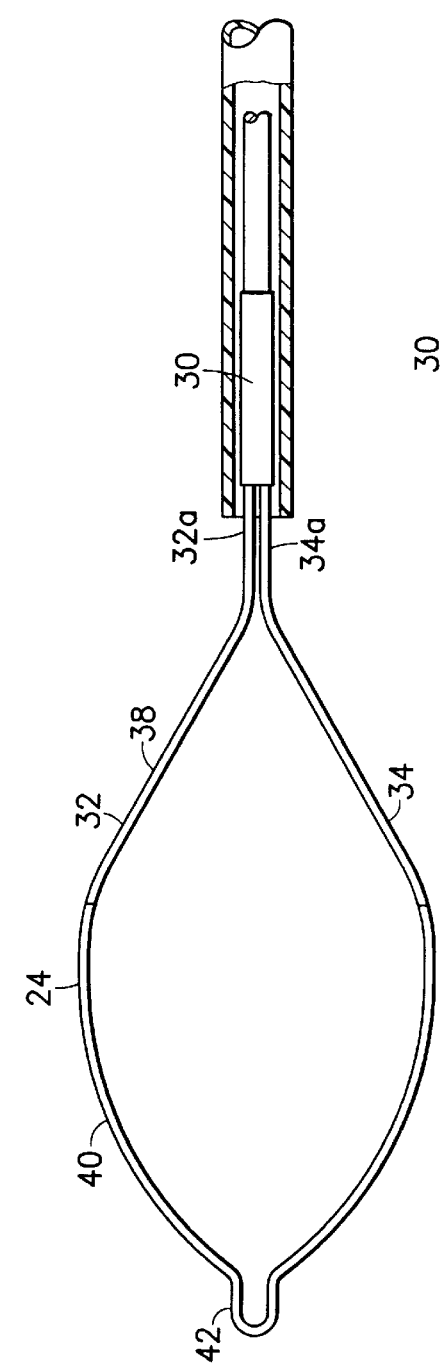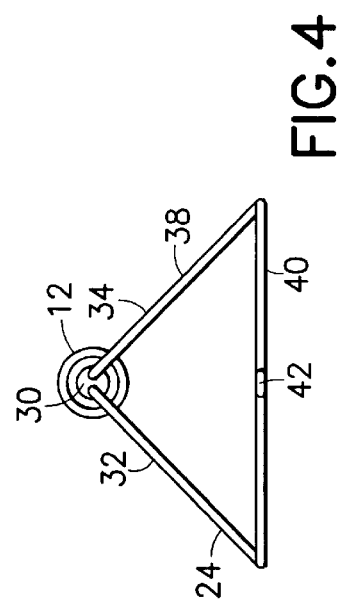

POLYPECTOMY SNARE INSTRUMENT

BACKGROUND OF THE INVENTION

1. Field of the Invention

This invention relates broadly to surgical instruments. More particularly, this invention relates to a surgical snare instrument for excising polyps.

2. State of the Art

Surgical snares instruments are used for the endoscopic removal of hypertrophic tissue growths within a body cavity, and particularly within the colon. Snare instruments generally include an elongate tubular member, such as a catheter sheath, a shaft extending through the tubular member, and an elastic wire (e.g., stainless steel or Nitinol) forming a loop movable distally and proximally within the tubular member. The loop can be opened by moving the loop beyond the distal end of the tubular member and closed by retraction into the tubular member, each effected by movement of the shaft relative to the sheath. A handle is provided at the proximal end of the instrument to facilitate this movement.

With the loop of the snare instrument in a retracted position, the distal end of the instrument is inserted through an endoscope into the gastrointestinal tract and moved toward a polyp or other tissue growth which is identified for removal from the wall of the tract. The handle of the instrument is then operated to expand the loop of the snare and an attempt is made to maneuver the loop to surround the polyp. If successful, the loop is then constricted about the polyp to excise it. Additionally, the snare instrument may be provided with cautery capability in order to limit bleeding and thereby enhance the polyp removal procedure.

It will be appreciated that manipulation of the loop of the snare instrument about the polyp is a difficult, and sometimes unattainable, task. The expanded snare loop often lies in a plane which is not conducive for maneuvering about the polyp along the colon wall. However, as the snare instrument is extended through a relatively central lumen of an endoscope to the locus of the polyp, and as the endoscope may be positioned centrally within the colon, it is difficult to direct the loop of the snare along the wall of the colon to ensnare the polyp. Therefore, the desired polyp retrieval often requires extensive effort and at times cannot be achieved with the snare instrument and a more invasive procedure may be required to remove the hypertrophic growth.

SUMMARY OF THE INVENTION

It is therefore an object of the invention to provide a surgical snare instrument having a tubular member and a snare loop extendable through and beyond the distal end of the tubular member, such that when the snare instrument is positioned with the snare loop extended beyond the distal end of the tubular member, the snare loop is oriented to facilitate engaging a polyp or other hypertrophic growth.

It is another object of the invention to provide a surgical snare instrument having a tubular member and a snare loop extendable through and beyond the distal end of the tubular member, such that when the snare loop is extended beyond the distal end of the tubular member, the snare loop is oriented substantially parallel yet non-axial with the tubular member.

It is a further object of the invention to provide a surgical snare instrument which has particular application in removing polpys in the gastrointestinal tract.

It is an additional object of the invention to provide a surgical snare instrument having a tubular member and a snare loop extendable through and beyond the distal end of the tubular member, where the snare loop is precisely controlled by a torqueable shaft.

In accord with these objects, which will be discussed in detail below, a surgical snare instrument is provided. The snare instrument includes an elongate tubular sheath having proximal and distal ends, a flexible shaft having proximal and distal ends extending through and axially movable relative to the sheath, a snare loop at the distal end of the shaft, and a handle assembly coupled to the proximal ends of the sheath and shaft for moving the shaft axially relative to the sheath. The snare loop is trained to have a proximal portion which extends along an angle or curve relative to the tubular member and a distal portion which is substantially parallel to the tubular member. As such, when the snare loop is axially moved beyond the distal end of the tubular member, the distal portion of the snare loop; i.e., that portion which is adapted to engage a polyp, is oriented substantially parallel, yet non-axial, with the tubular member. The handle assembly is preferably provided with cautery capability to provide a cautery current to the shaft and the snare loop at the distal end thereof.

According to one embodiment of the invention, the shaft is torqueable, preferably comprised of a multifilament twisted and drawn or swaged cable. In addition, the handle is preferably adapted to axially rotate the shaft, and consequently the snare loop, at the distal end of the shaft.

According to another embodiment of the invention, the snare loop is additionally provided with a net element, preferably made from a PTFE fabric, adapted to capture a polyp severed by the snare loop.

In use, the user locates the distal end of the undeployed snare instrument in the colon to a location slightly beyond a polyp on the wall of the colon. The user then actuates the handle assembly to cause the shaft to be moved axially distally relative to the tubular member and the snare loop to be extended out of the tubular member. The distal portion of the snare loop extends in a parallel, yet non-axial, manner in relation to the axis of the tubular member and rests on the wall of the colon distal of the polyp. That is, the distal portion of the snare loop is adapted to automatically move to the root level of the stalk of the polyp, making the subsequent ensnarement of the polyp relatively quick and easy. The snare loop is then rotated (if required) and moved proximally to cause the snare loop to ensnare the polyp. The user then preferably applies a cautery current to the snare loop while tightly closing the snare loop about the polyp such that the polyp is excised and the tissue thereabout is cauterized. The snare loop with polyp held therein, particularly facilitated in the embodiment utilizing a net element, is withdrawn into the tubular member and the instrument is removed from the colon.

Additional objects and advantages of the invention will become apparent to those skilled in the art upon reference to the detailed description taken in conjunction with the provided figures.

BRIEF DESCRIPTION OF THE DRAWINGS

FIG. 2 is an enlarged partial broken side view of a distal end of the first embodiment of the snare instrument;

FIG. 3 is an enlarged partial broken top view of the distal end of the first embodiment of the snare instrument of the invention;

FIG. 4 is an enlarged distal end view of the first embodiment of the snare instrument according to the invention;

DETAILED DESCRIPTION OF THE PREFERRED EMBODIMENTS

Figure 1:
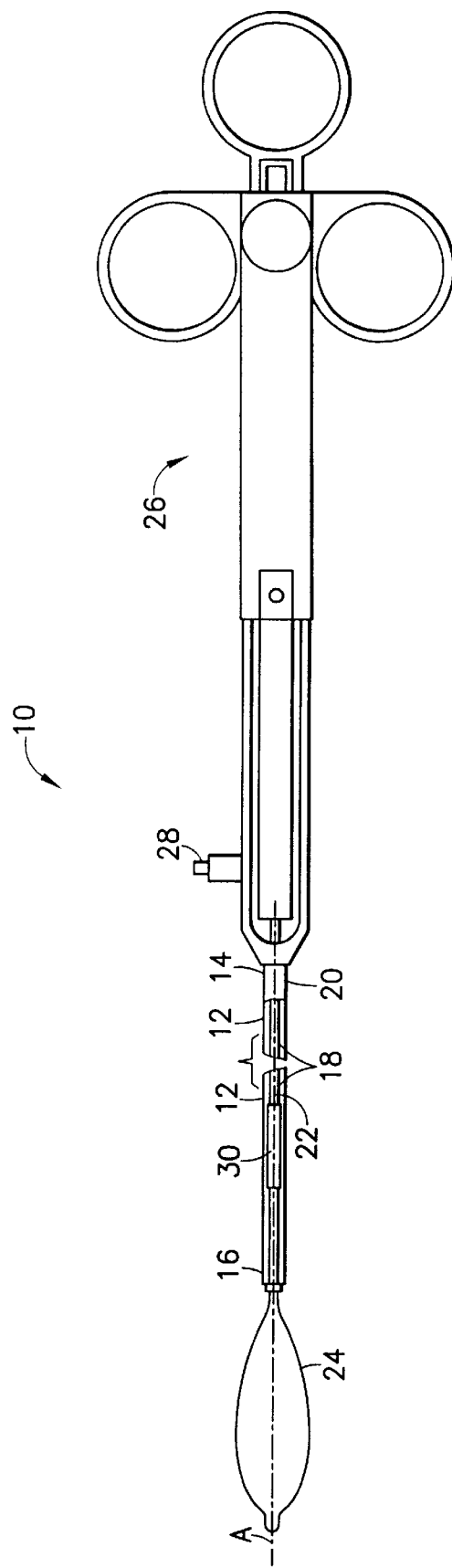
FIG. 1 is a broken side elevation of a snare instrument according to the invention.

Turning now to FIG. 1, a surgical snare instrument 10 according to the invention is shown. The snare instrument 10 includes an elongate flexible tubular sheath 12 having a proximal end 14 and a distal end 16 and a preferably electrically conductive flexible shaft 18 having a proximal end 20 and a distal end 22 extending through and axially movable relative to the sheath 12. A snare loop 24 is mechanically and conductively coupled to the distal end 22 of shaft 18 at 30, preferably adjacent the distal end 16 of the sheath 12. A handle assembly 26 is also provided for moving the shaft 18 relative to the sheath 12 such that the snare loop 24 is extendable beyond the distal end 16 of the sheath 12. A cautery connector 28 is preferably provided to the handle 26 and conductively coupled, e.g., via a brush connector (not shown), to the shaft 18 such that the shaft is permitted axial movement while maintaining such conductive coupling.

The shaft 18 is preferably comprised of a multifilament twisted and drawn or swaged cable. The filaments of the multifilament twisted and drawn or swaged cable are preferably either stainless steel, nickel-titanium alloy, or a combination of the two. The construction of multifilament twisted and drawn or swaged cables for a medical device is generally disclosed in co-owned and co-pending U.S. Ser. No. 08/856,571, and multifilament twisted and drawn or swaged cables comprised at least in part of nickel-titanium alloy are particularly disclosed in co-owned and co-pending U.S. Ser. Nos. 09/044,203, 09/060,969, and 09/087,476, all of which are hereby incorporated by reference herein in their entireties. With the multifilament twisted and drawn or swaged cable, the shaft 18 is highly controllably torqueable. In view of the torqueability of the shaft, it will be appreciated that the handle assembly 26 may be adapted to rotate the shaft 18 and snare loop 24 relative to the sheath 12. Such a handle assembly is disclosed in co-owned and co-pending U.S. Ser. No. 09/237,420, entitled "Polypectomy Snare Instrument with Rotatable Shaft" and filed on Jan. 26, 1999, which is hereby incorporated by reference herein in its entirety.

Turning now to FIGS. 2 through 4, the snare loop 24 is preferably also formed from a length of multifilament twisted and drawn or swaged cable, as described above, or another resilient cable or wire. The snare loop 24 includes two sides 32, 34 having first and second ends 32a, 34a attached at 30 to the distal end 22 of the shaft 18, for example, by welding, soldering or crimping. Alternatively, the shaft may be formed from a resilient cable or wire which has first and second ends proximally twined and an untwined looped distal portion forming the snare loop; that is, the snare loop is integral with the shaft. As yet another alternative, the two sides of the snare loop may be formed from separate wire or cable elements coupled together at their proximal and distal ends to form the snare loop therebetween.

The snare loop 24 is preferably cold-formed to the desired configuration. In accord with the invention, one preferred configuration of the snare loop 24 which, when extended out of the sheath includes a proximal portion 38 which is biased to be angled off-axis relative to the axis A of the distal end of the tubular member 12, with arms 32, 34 of the loop preferably laterally diverging. As such, the arms 32, 34 of the proximal portion 38 substantially extend within a plane which is angled relative to the distal end of the tubular member 12, as illustrated in FIGS. 2 and 4. The snare loop 24 also includes a distally-directed distal portion 40 which is biased to be angled relative to the proximal portion 38 such that the distal portion is substantially parallel to the axis A of the distal end of the tubular member 12. The distalmost portion (or apex) of the loop 24 is preferably formed with a U-shaped catch 42 adapted for engaging the stem of a polyp. It will be appreciated that since the snare loop 24 is flexible, it assumes a substantially straight configuration when held in the sheath 12, and only assumes its desired configuration when extended out of the sheath.

Figure 5:
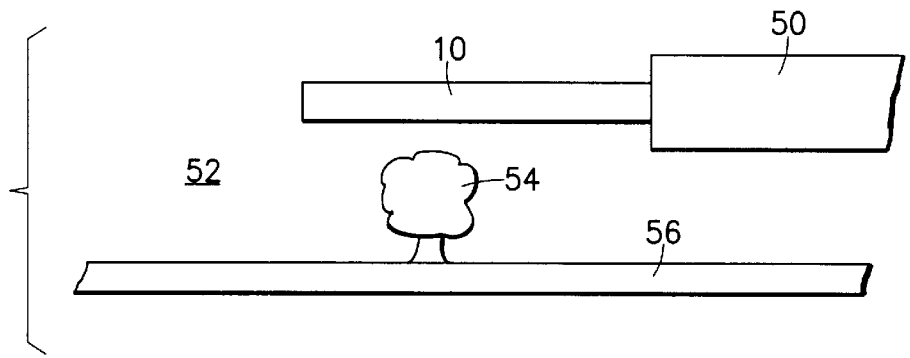
FIGS. 5 through 9 illustrate the in vivo use of the snare instrument of the invention.
Figure 6:
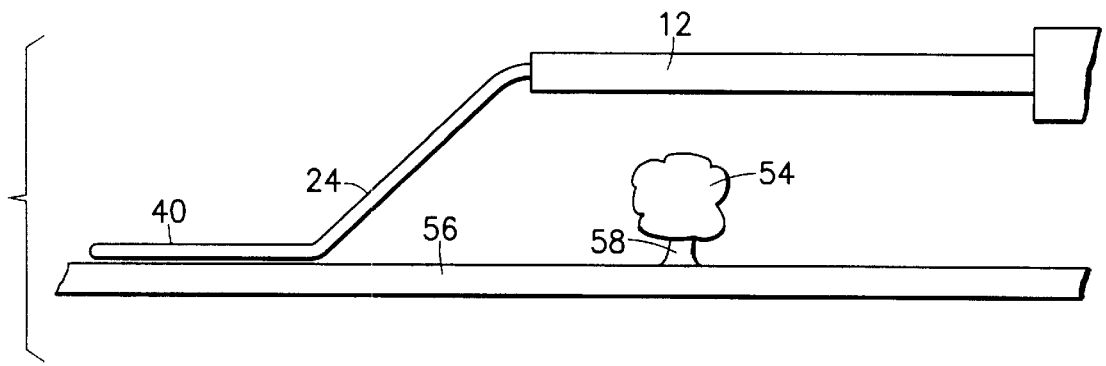
Figure 7:
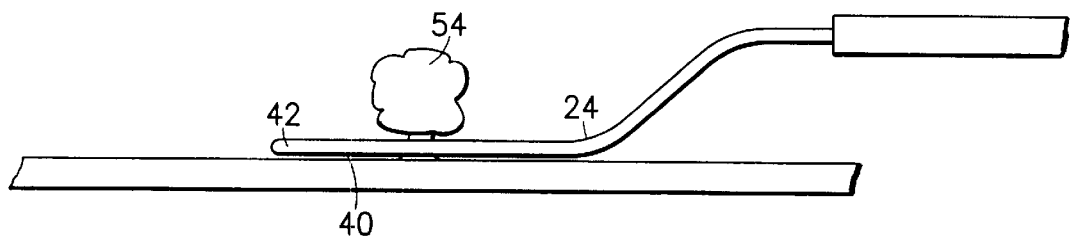
Figure 8:
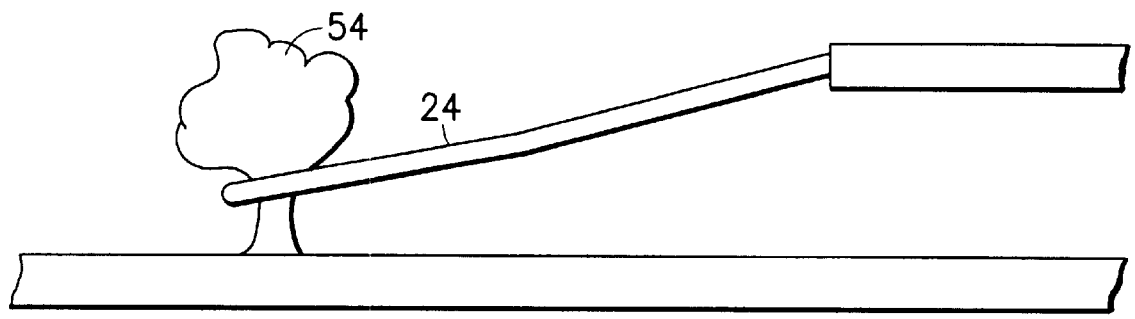
Figure 9:
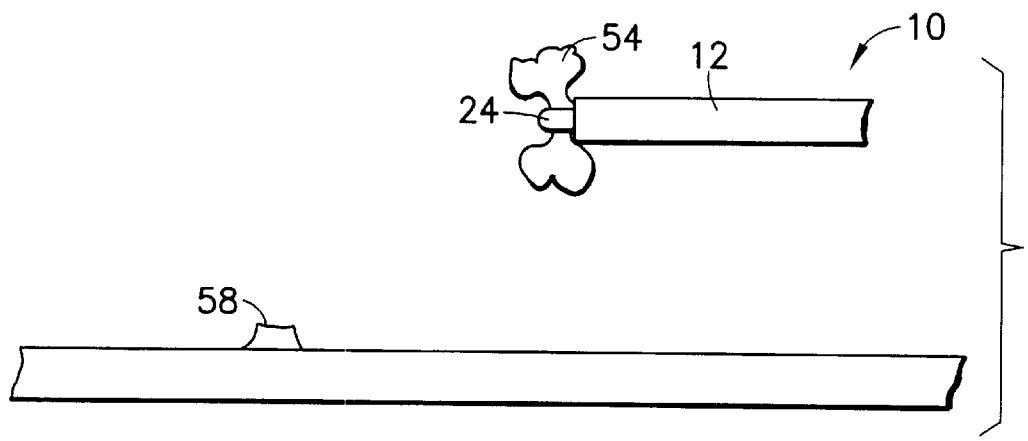

Referring now to FIGS. 1 and 5 through 9, in use, a user inserts the snare instrument 10 into an endoscope 50 located in the colon 52, utilizes the scope to identify for excision and retrieval a polyp 54 on the wall 56 of the colon, and maneuvers the distal end of the undeployed snare instrument in the colon to a location slightly beyond the polyp (FIG. 5). The user then actuates the handle assembly 26 of the instrument 10 to cause the shaft 18 to be moved axially distally relative to the tubular member to move the snare loop 24 out of the tubular member 12 (FIGS. 1 and 6). The distally-directed distal portion 40 of the snare loop 24 extends in parallel, yet non-axial, in relation to the axis of the tubular member 12 and rests on or adjacent the wall 56 of the colon distal of the polyp 54. That is, the distal portion 40 of the snare loop 24 is adapted to automatically move to the root level of the stalk 58 of the polyp 54, making the subsequent ensnarement of the polyp relatively quick and easy. The snare loop 24 is then rotated by rotation of the handle, if required to rotationally align the snare loop with the polyp, and then moved proximally to cause the snare loop, and particularly the polyp catch 42, to ensnare the polyp 54 (FIG. 7). The user then preferably applies a cautery current to the snare loop 24 while tightly closing the snare loop about the polyp 54 such that the polyp is excised and the tissue at the stalk 58 is cauterized (FIGS. 8 and 9). The snare loop 24 with polyp 54 held therein is withdrawn into the tubular member 12 and the instrument 10 is removed from the colon (FIG. 9).

Figure 10:
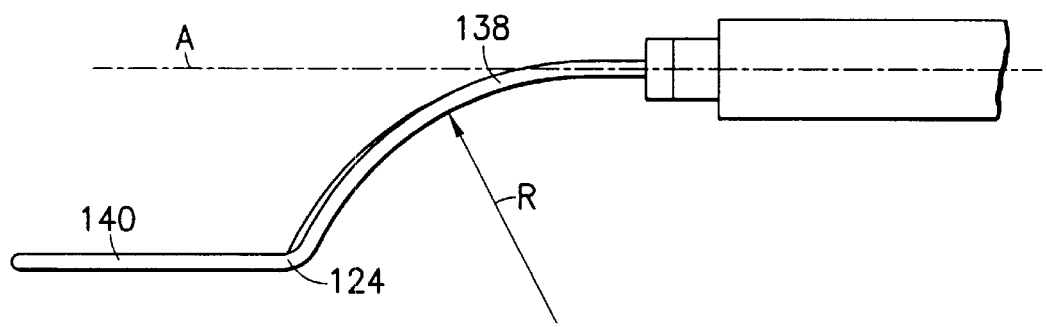
FIG. 10 is an enlarged broken side elevation of the distal end of a second embodiment of the snare instrument according to the invention.

It will be appreciated that several variations of the configuration of the snare loop according to the invention may also be used on the snare instrument. Turning now to FIG. 10, according to one variation, an alternate snare loop 124 is shown. The snare loop 124 includes a proximal portion 138 which curves along a radius R away from the axis A of the tubular member. The distal portion 140 of the snare loop 124 is preferably configured and oriented as described above with reference to the first embodiment of the invention.

Figure 11:
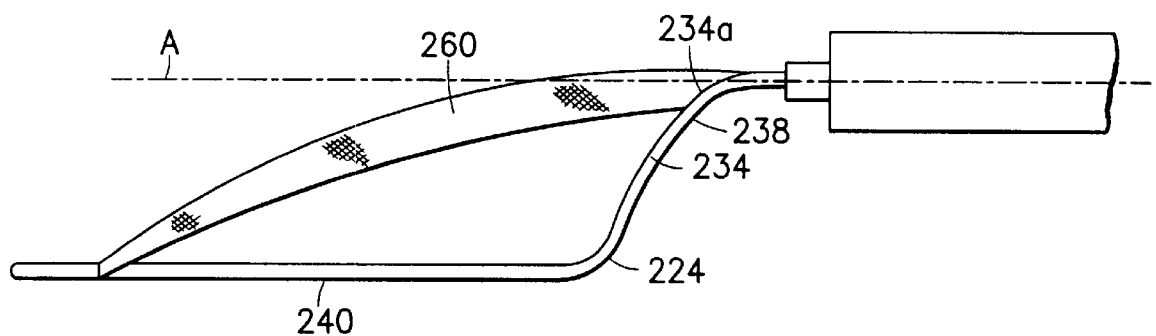
FIG. 11 is an enlarged broken side elevation of the distal end of a third embodiment of the snare instrument according to the invention.
Figure 12:
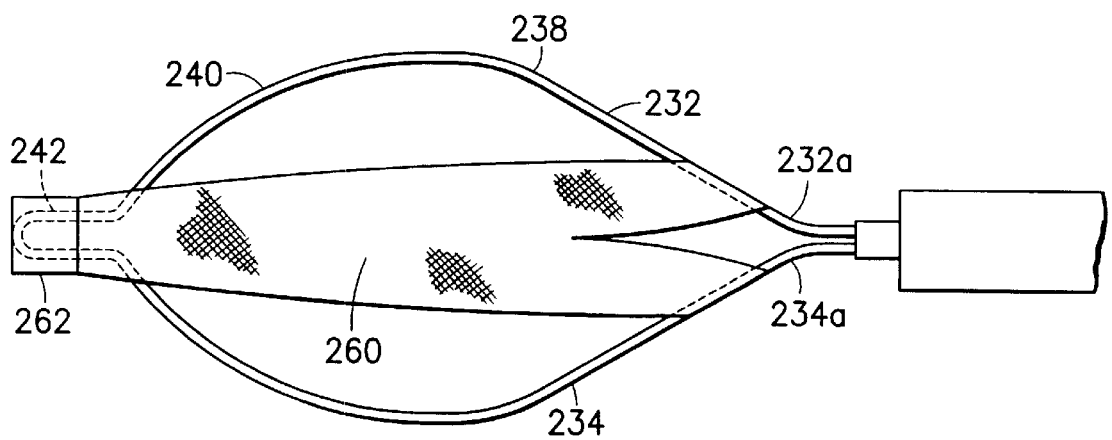
FIG. 12 is an enlarged broken top view of the third embodiment of the snare instrument.

Turning now to FIGS. 11 and 12, a third embodiment of a snare loop 224 for a snare instrument is shown. The snare loop 224 includes a proximal portion 238 biased to be non-axial relative to the axis A of the distal end of the tubular member and a distal 240 portion biased relative to the proximal portion to extend relatively parallel to the axis A of the tubular member. The snare loop 224 is provided with a net element 260, preferably made from a PTFE fabric or other heat resistant fabric. The net element 260 is preferably coupled to the proximal portions 232a, 234a of the sides 232, 234 and also at the distal portion adjacent or at the catch 242. A clip 262 may be applied at the catch 242 to secure the net element 260 thereto and the net element may be adhered, sutured, or otherwise attached at the proximal portions of the sides of the snare loop.

The embodiment of FIGS. 11 and 12 is used as described above with reference to the first embodiment of the invention. However, it will be appreciated that the net element facilitates capture and retrieval of a polyp severed by the snare loop. Furthermore, the heat resistant property of the fabric of the net element prevents the net element from being damaged by the cautery current.

There have been described and illustrated herein several embodiments of a surgical snare instrument. While particular embodiments of the invention have been described, it is not intended that the invention be limited thereto, as it is intended that the invention be as broad in scope as the art will allow and that the specification be read likewise. Thus, while the proximal portion of the snare loop has been shown to angle or curve relative to the shaft, it will be appreciated that the proximal portion of the snare loop may take yet another path to the distal portion which is oriented substantially parallel yet non-axial with the axis of the tubular member. For example, the proximal portion may be formed with a plurality of curves or bends such that the distal portion is oriented in accord with the invention. In addition, while the snare loop has been described as being formed by cold working, it will be appreciated that it may be formed according to other techniques for causing shape memory or superelastic materials to assume a desired configuration. Moreover, the snare loop is preferably a supple and resilient cable, thereby reducing the tendency of the snare loop to lift off the polyp and facilitating the snare loop being drawn into the sheath with the polyp upon retraction of the snare loop relative to the sheath. However, a relatively stiff and resilient cable may be preferred in certain applications. Furthermore, while the snare instrument has been described for use in the gastrointestinal tract, it will be appreciated that it can be used elsewhere within the body, e.g., the uterus or urinary tract. It will therefore be appreciated by those skilled in the art that yet other modifications could be made to the provided invention without deviating from its spirit and scope as claimed.

What is claimed is:

1. A surgical snare instrument, comprising:
   a) an elongate flexible tubular sheath having proximal and distal ends, said distal end defining a longitudinal axis;
   b) a flexible shaft having proximal and distal ends, said flexible shaft extending through and axially movable relative to said sheath;
   c) a snare loop provided at said distal end of said flexible shaft, wherein when said snare loop extends beyond said distal end of said tubular sheath in a first position said snare loop has a proximal portion which extends non-axially relative to said longitudinal axis and a distally-directed distal portion which is angled relative to said proximal portion and extends substantially parallel to said longitudinal axis; and
   d) a handle assembly coupled to said shaft and said sheath, said handle assembly configured to move at least one of said shaft and said sheath axially relative to the other.

2. A surgical snare instrument according to claim 1, wherein:
   said distal portion of said snare loop extends non-axially relative to said longitudinal axis.

3. A surgical snare instrument according to claim 1, wherein:
   when said flexible shaft is moved relative to said flexible sheath such that said snare loop extends substantially entirely within said sheath in a second position, said proximal and distal portions of said snare loop extend substantially axially relative to said longitudinal axis.

4. A surgical snare instrument according to claim 1, wherein:
   said proximal portion of said snare loop lies substantially within a plane.

5. A surgical snare instrument according to claim 1, wherein:
   said proximal portion of said snare loop is curved along a radius of curvature.

6. A surgical snare instrument according to claim 1, wherein:
   said snare loop is constructed of a multifilament twisted and drawn or swaged cable.

7. A surgical snare instrument according to claim 6, wherein:
   said multifilament twisted and drawn or swaged cable includes at least one of a stainless steel filament and a nickel-titanium alloy filament.

8. A surgical snare instrument according to claim 1, wherein:
   said handle assembly includes means for applying a cautery current to said flexible shaft.

9. A surgical snare instrument according to claim 1, wherein:
   said snare loop is provided with a net element.

10. A surgical snare instrument according to claim 9, wherein:
    said net element is heat resistant.

11. A surgical snare instrument according to claim 10, wherein:
    said net element comprises a PTFE fabric.

12. A surgical snare instrument according to claim 1, wherein:
    said flexible shaft is constructed of a multifilament twisted and drawn or swaged cable.

13. A surgical snare instrument according to claim 12, wherein:
    said handle assembly is adapted to axially rotate said flexible shaft relative to said tubular sheath.

14. A surgical snare instrument, comprising:
    a) an elongate flexible tubular sheath having proximal and distal ends, said distal end having a longitudinal axis;
    b) a flexible shaft having proximal and distal ends, said flexible shaft extending through and axially movable relative to said sheath;
    c) a snare loop provided at said distal end of said flexible shaft, said snare loop having a proximal portion biased to extend non-axially relative to said longitudinal axis and a distally-directed distal portion biased to extend substantially parallel to said longitudinal axis; and
    d) a handle assembly coupled to said sheath and said flexible shaft and configured to move at least one of said shaft and said sheath axially relative to the other.

15. A surgical snare instrument according to claim 14, wherein:
    said proximal portion of said snare loop lies substantially within a plane.

16. A surgical snare instrument according to claim 14, wherein:
    said proximal portion of said snare loop is curved along a radius of curvature.

17. A surgical snare instrument according to claim 14, wherein:

said snare loop is constructed of a multifilament twisted and drawn or swaged cable.

18. A surgical snare instrument according to claim 14, wherein:

said handle assembly includes means for applying a cautery current to said flexible shaft.

19. A surgical snare instrument according to claim 14, wherein:

said snare loop is provided with a net element.

20. A surgical snare instrument according to claim 19, wherein:

said net element is heat resistant.

21. A surgical snare instrument according to claim 20, wherein:

said net element comprises a PTFE fabric.

22. A surgical snare instrument according to claim 14, wherein:

said flexible shaft is constructed of a multifilament twisted and drawn or swaged cable.

23. A surgical snare instrument according to claim 22, wherein:

said handle assembly is adapted to axially rotate said flexible shaft relative to said tubular sheath.

* * * * *